United States Patent
Kang et al.

(10) Patent No.: US 9,771,555 B2
(45) Date of Patent: Sep. 26, 2017

(54) CANINE AMNIOTIC MEMBRANE-DERIVED MULTIPOTENT STEM CELLS

(71) Applicant: Kang Stem Biotech, Co., LTD., Seoul (KR)

(72) Inventors: Kyung Sun Kang, Seoul (KR); Min Soo Seo, Daegu (KR); Sang Bum Park, Seoul (KR)

(73) Assignee: KANG STEM BIOTECH, CO., LTD., Seoul (KR)

( * ) Notice: Subject to any disclaimer, the term of this patent is extended or adjusted under 35 U.S.C. 154(b) by 53 days.

(21) Appl. No.: 14/363,145

(22) PCT Filed: Dec. 6, 2012

(86) PCT No.: PCT/KR2012/010538
§ 371 (c)(1),
(2) Date: Jun. 5, 2014

(87) PCT Pub. No.: WO2013/085303
PCT Pub. Date: Jun. 13, 2013

(65) Prior Publication Data
US 2014/0322182 A1  Oct. 30, 2014

(30) Foreign Application Priority Data
Dec. 6, 2011 (KR) ........................ 10-2011-0129818

(51) Int. Cl.
| | |
|---|---|
| *A61K 35/50* | (2015.01) |
| *C12N 5/074* | (2010.01) |
| *C12N 5/0735* | (2010.01) |
| *C12N 5/0775* | (2010.01) |
| *C12N 5/079* | (2010.01) |
| *C12N 5/077* | (2010.01) |
| *G01N 33/569* | (2006.01) |

(52) U.S. Cl.
CPC ............ *C12N 5/0606* (2013.01); *A61K 35/50* (2013.01); *C12N 5/0618* (2013.01); *C12N 5/0653* (2013.01); *C12N 5/0654* (2013.01); *C12N 5/0655* (2013.01); *C12N 5/0668* (2013.01); *G01N 33/56966* (2013.01)

(58) Field of Classification Search
CPC ..... C12N 5/0606; C12N 5/0668; A61K 35/50
See application file for complete search history.

(56) References Cited

U.S. PATENT DOCUMENTS

2009/0238801 A1* 9/2009 Woodbury et al. .......... 424/93.7

FOREIGN PATENT DOCUMENTS

| KR | 100818214 B1 | 3/2008 |
|---|---|---|
| KR | 1020110022759 A | 3/2011 |

OTHER PUBLICATIONS

Kim et al., Ex vivo characteristics of human amniotic membrane-derived stem cells. Cloning and Stem Cells, vol. 9, No. 4 (2007) pp. 581-594.*
11885-DMEM, low glucose, pyruvate. Datasheet [online]. ThermoScientific, 2015 [retrieved on Dec. 28, 2015]. Retrieved from the Internet: <URL: http://www.thermofisher.com/us/en/home/technical-resources/media-formulation.48.html>.*
Cheng et al., High glucose-induced reactive oxygen species generation promotes stemness in human adipose-derived stem cells. Cryotherapy, vol. 18 (2016) pp. 371-383.*
Insausti, CL et al., "The amniotic membrane as a source of stem cells" (Jan. 2010) Histol Histopathol 25:1 pp. 91-98.
Jiang, Yuehua at al., "Multipotent progenitor cells can be isolated from postnatal murine bone marrow, muscle, and brain" (2002) Experimental Hematology 30 pp. 896-904.
Jiang, Yuehua et al., "Pluripotency of mesenchymal stem cells derived from adult marrow" (Jul. 4, 2002) Nature 418 pp. 41-49.
Park, Sang-Bum et al., "Isolation and Characterization of Canine Amniotic Membrane-Derived Multipotent Stem Cells" (2012) PLoS ONE 7(9):e44693. doi:10.1371/journal.pone.0044693.
Sampaolesi, Maurilio et al., "Cell Therapy of α-Sarcoglycan Null Dystrophic Mice Through Intra-Arterial Delivery of Mesoangioblasts" (2003) Science 301, 487 DOI: 10.1126/science.1082254.
Toma, Jean G. et al., "Isolation of multipotent adult stem cells from the dermis of mammalian skin" (Sep. 2001) Nature Cell Biology vol. 3 pp. 778-784.
Verfaillie, Catherine M., "Adult stem cells: assessing the case for pluripotency" (Nov. 2002) TRENDS in Cell Biology vol. 12 No. 11 pp. 502-508.

* cited by examiner

*Primary Examiner* — Kara Johnson
(74) *Attorney, Agent, or Firm* — Chainey P. Singleton; Edwin S. Flores; Chalker Flores, LLP

(57) ABSTRACT

The present invention relates to canine amniotic membrane-derived multipotent stem cells (cAM-MSCs) and preparation method thereof. More particularly, the present invention relates to canine amniotic membrane-derived multipotent stem cells, which show negative immunological properties on human markers CD3, CD11c, CD28, CD34, CD38, CD41a, CD45, and CD62L and positive immunological properties on human markers CD90 and CD105, and have the ability to be maintained in an undifferentiated state for 20 passages or more and the ability to be differentiated into fat, bones, nerves, cartilage, etc.

15 Claims, 10 Drawing Sheets

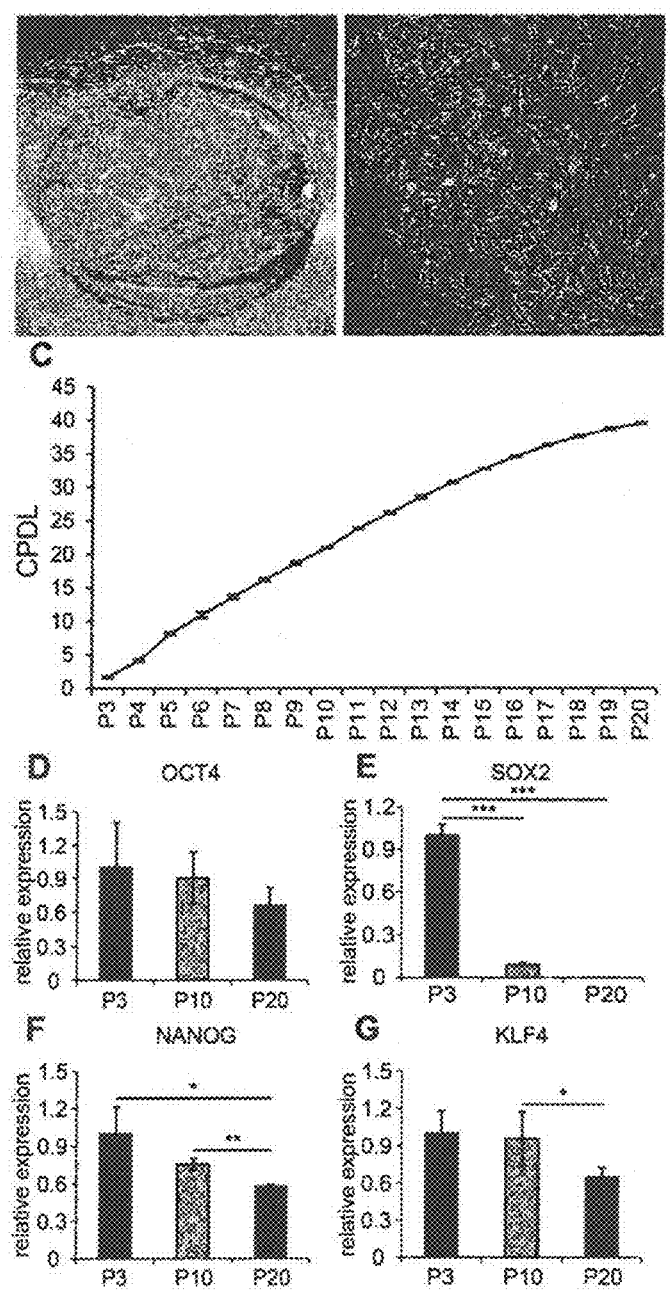

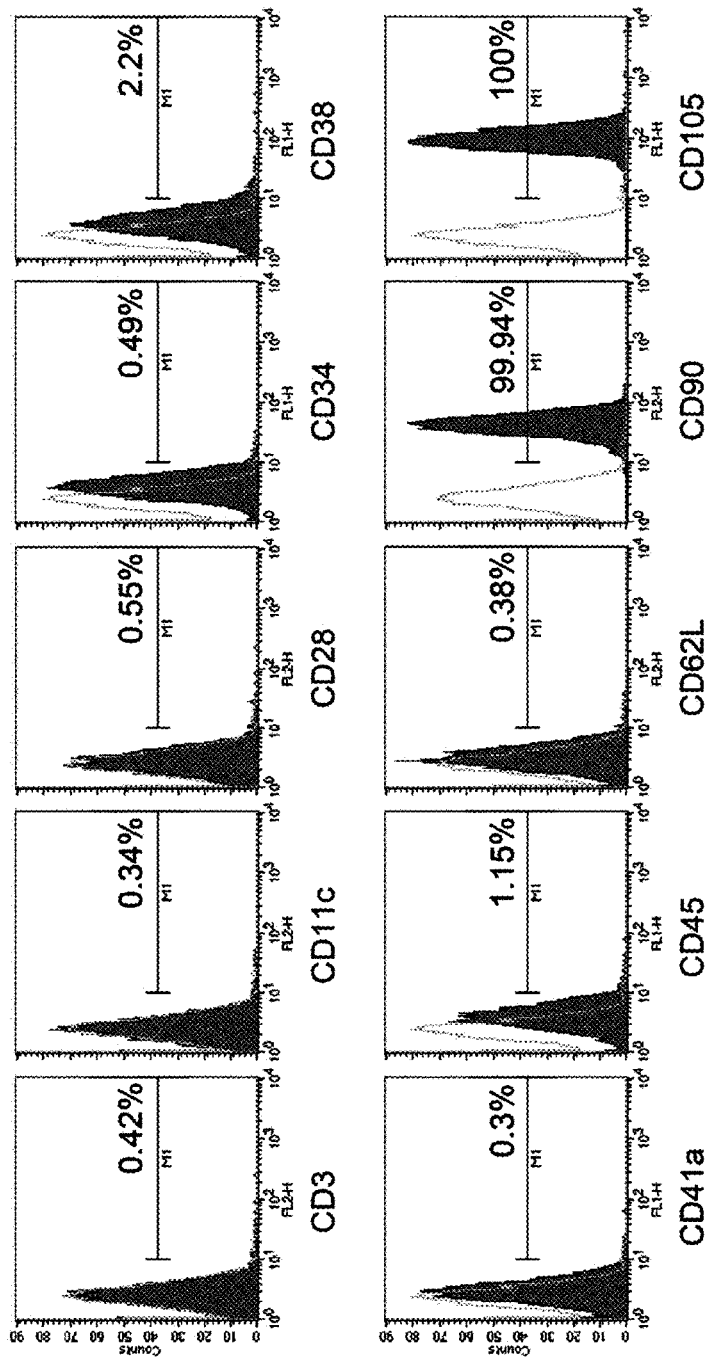
[Figure 2]

[Figure 3]
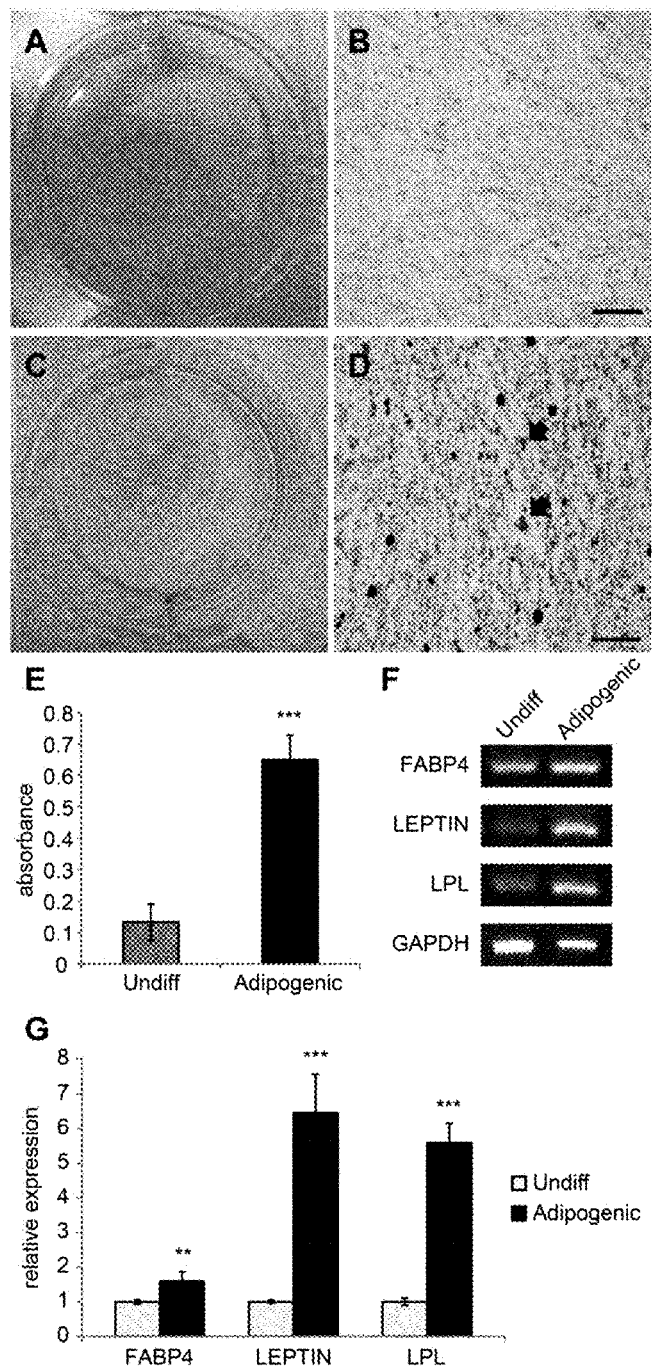

[Figure 4]
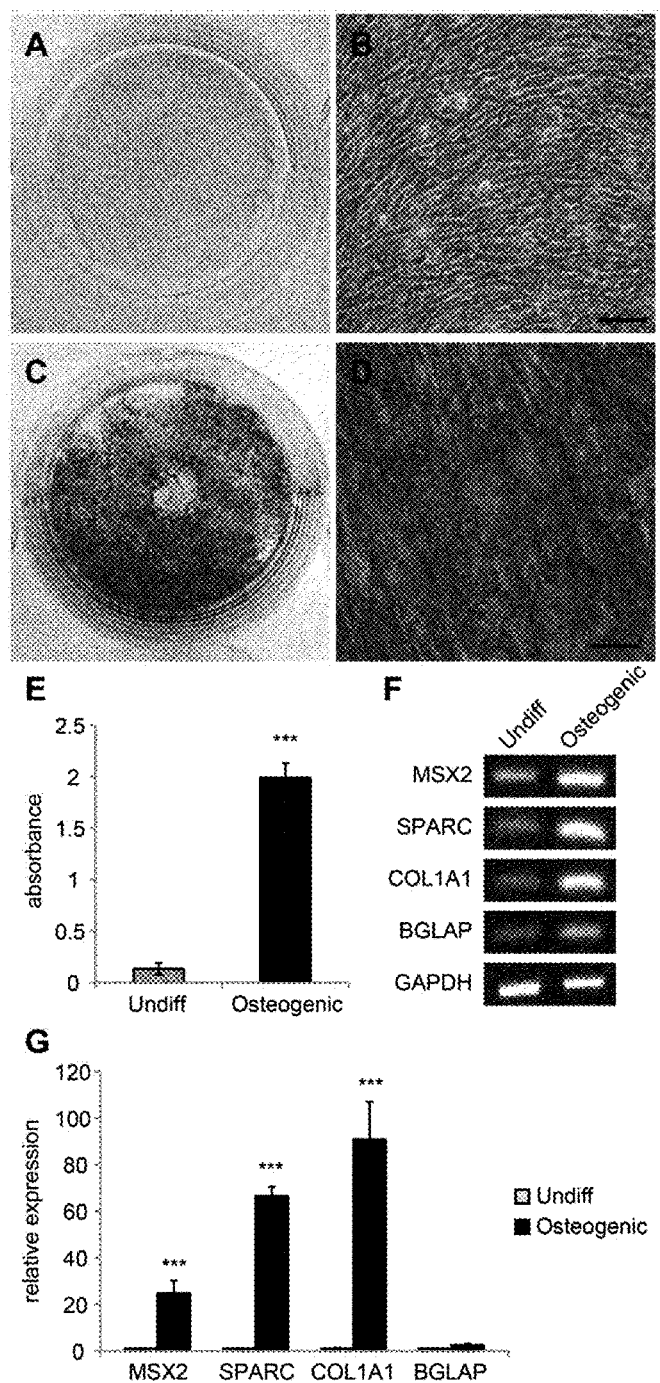

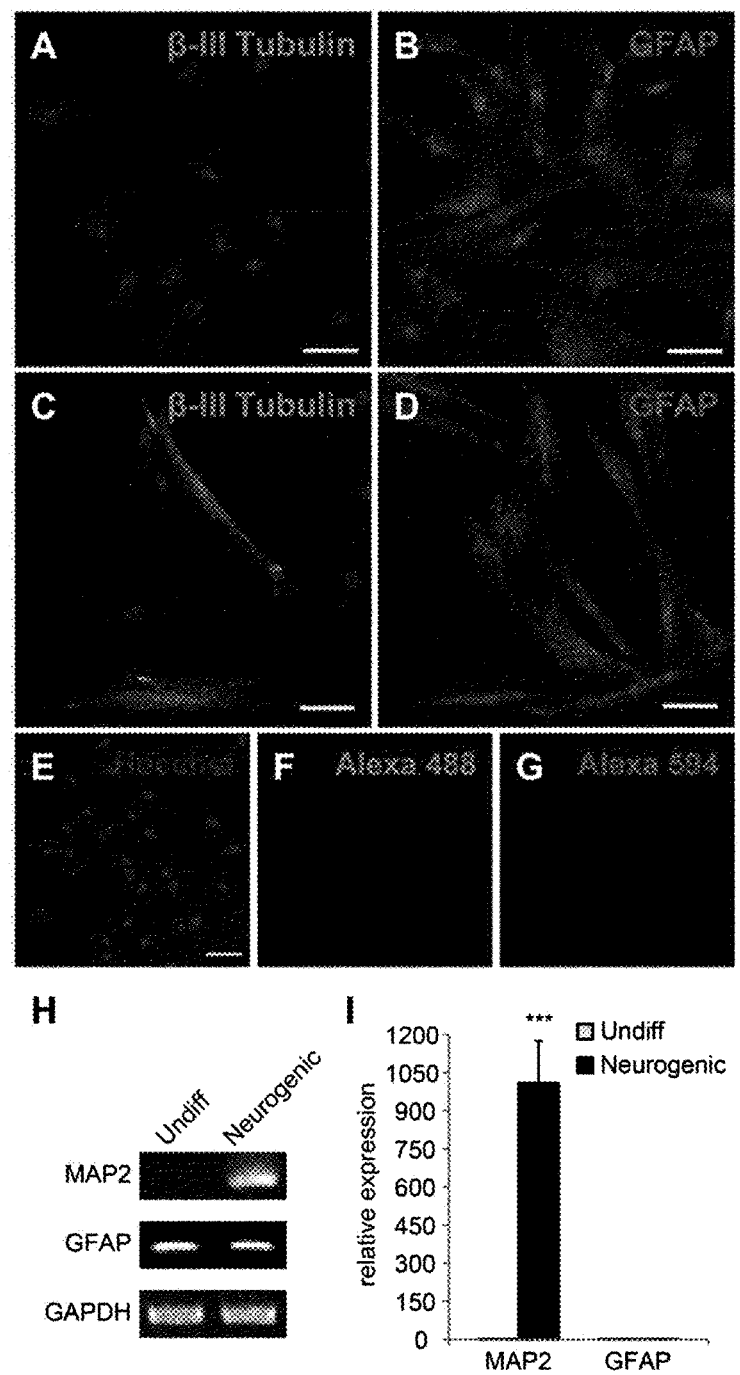
[Figure 5]

[Figure 6]
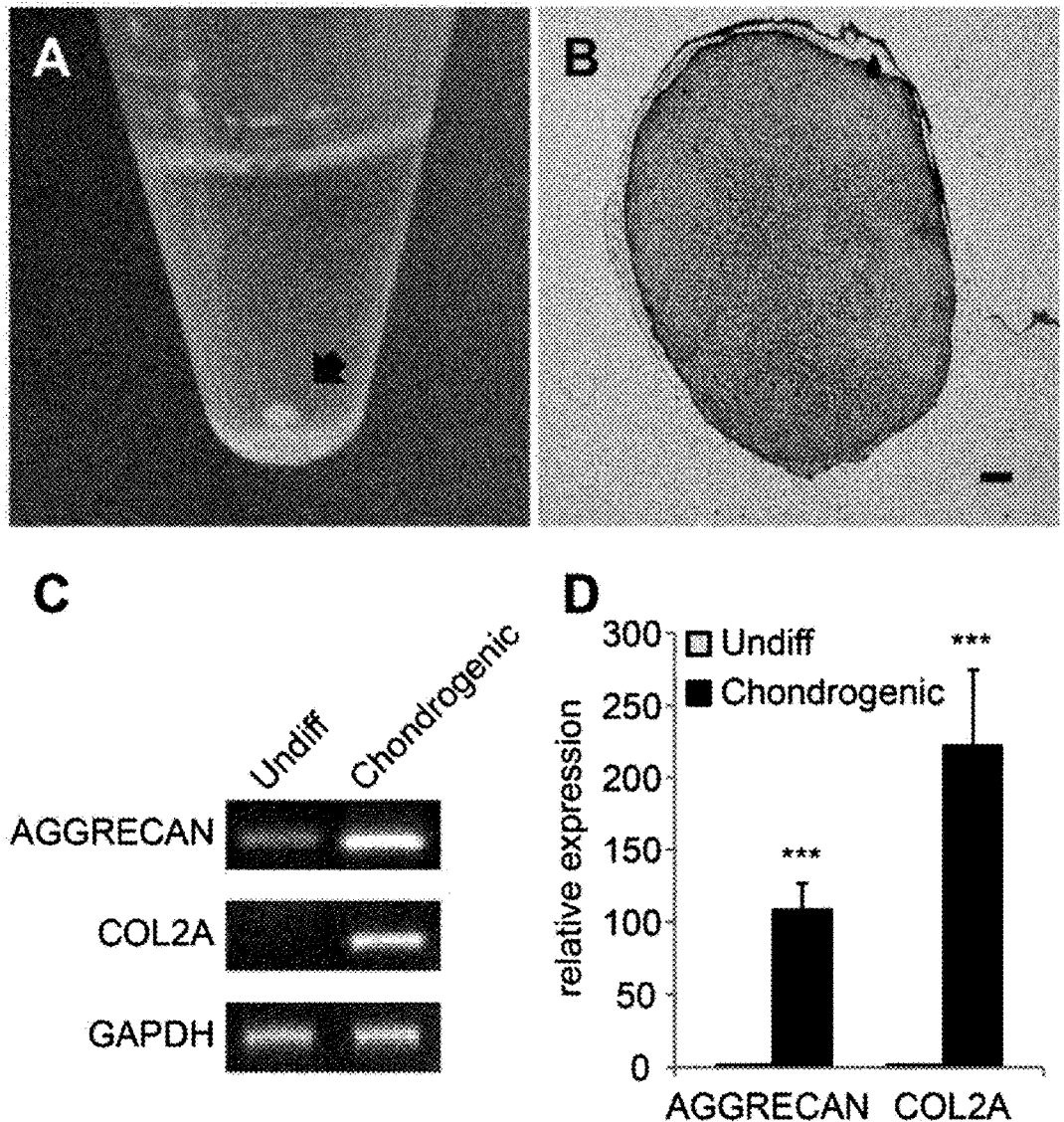

[Figure 7]
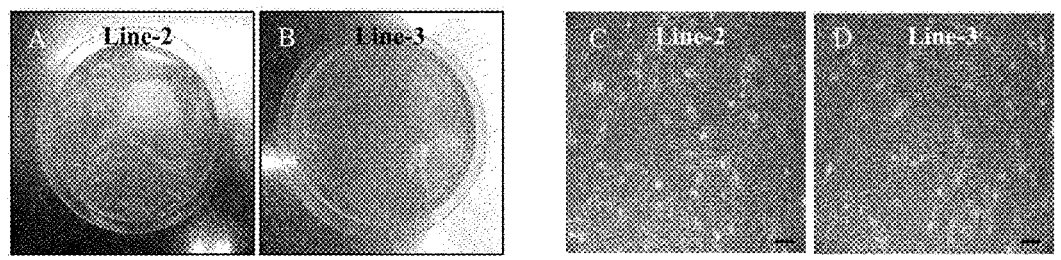
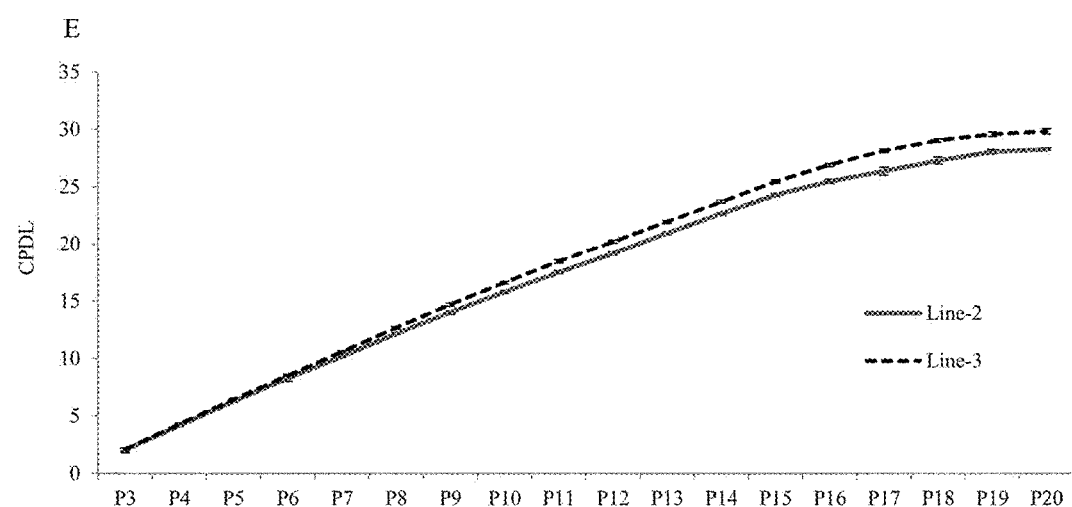

[Figure 8]
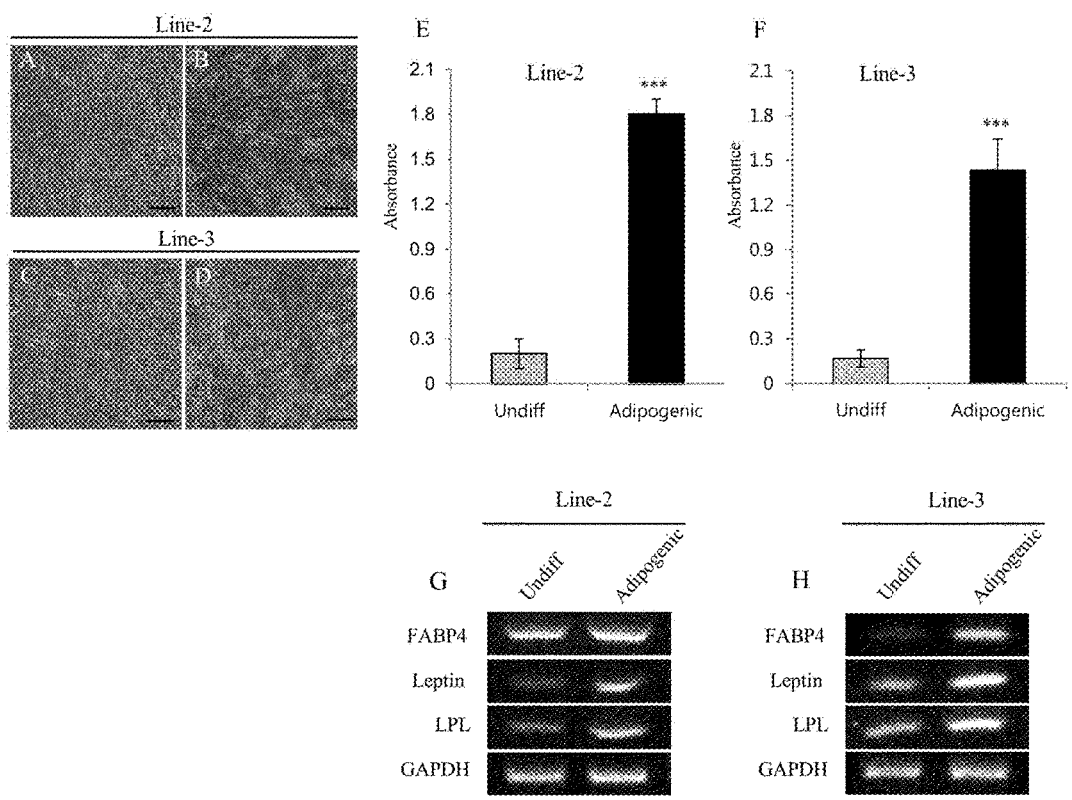

[Figure 9]
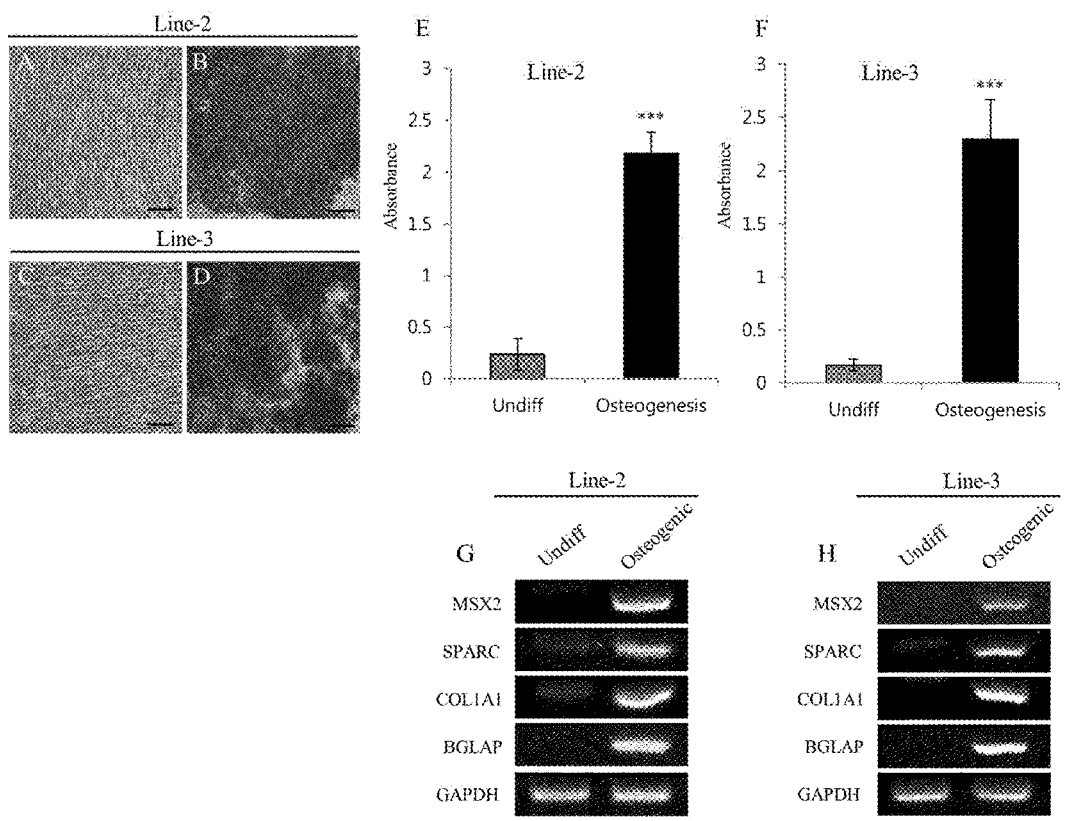

[Figure 10]
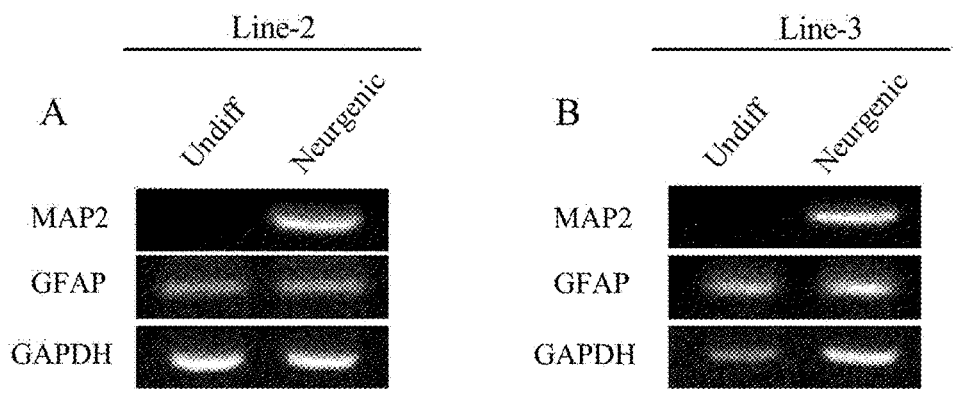
[Figure 11]
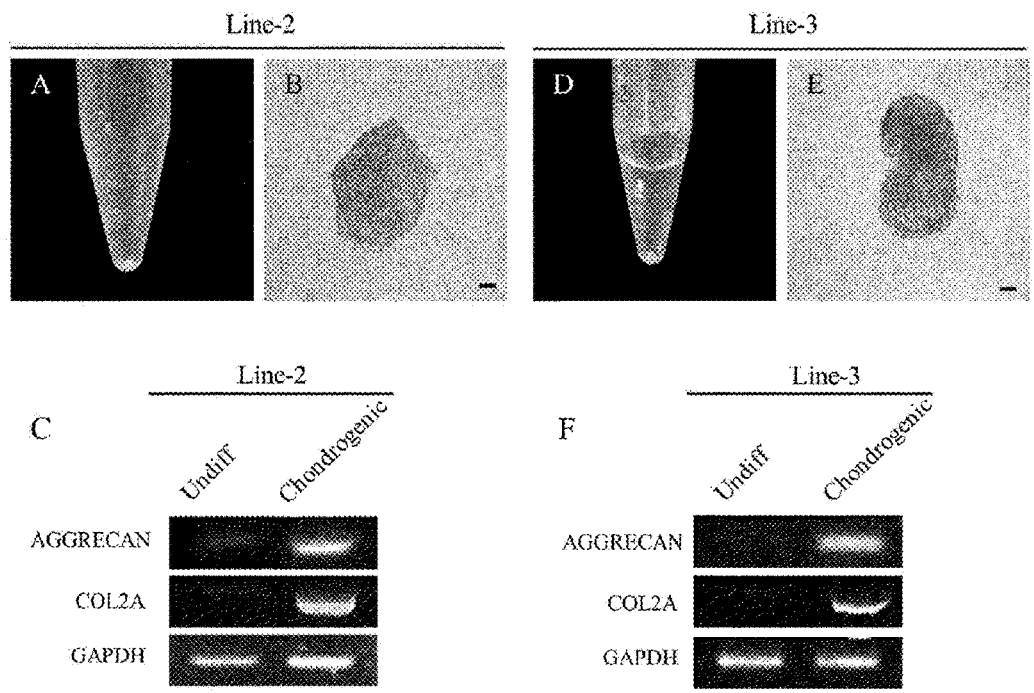

CANINE AMNIOTIC MEMBRANE-DERIVED MULTIPOTENT STEM CELLS

CROSS-REFERENCE TO RELATED APPLICATIONS

This application is the National Stage of International Application No. PCT/KR2012/010538, filed on 6 Dec. 2012 claiming the priority of KR 10-2011-0129818 filed on 6 Dec. 2011, the content of each of which is incorporated by reference herein.

TECHNICAL FIELD

The present invention relates to canine amniotic membrane-derived multipotent stem cells (cAM-MSCs) and a preparation method thereof. More particularly, the present invention relates to canine amniotic membrane-derived multipotent stem cells, which show negative immunological properties on human markers CD3, CD11c, CD28, CD34, CD38, CD41a, CD45, and CD62L and positive immunological properties on human markers CD90 and CD105, and have the ability to be maintained in an undifferentiated state for 20 passages or more and the ability to be differentiated into fat, bones, nerves, cartilage, etc.

BACKGROUND ART

Biotechnology in the 21$^{st}$ century presents the possibility of new solutions to food, environment and health problems, with the ultimate object of promoting human prosperity. In recent years, the technology of using stem cells has been considered as a new way to treat incurable diseases. Formerly, organ transplantation, gene therapy, etc., were proposed for the treatment of incurable human diseases, but their use has not been achieved efficiently due to immunorejection, a small supply of organs, and insufficient knowledge of genes.

For this reason, with increasing interest in stem cell research, it has been recognized that totipotent stem cells having the ability to form all organs by proliferation and differentiation can not only treat most diseases but also fundamentally heal organ injuries. Also, many scientists have suggested the applicability of stem cells for the regeneration of all the organs and the treatment of incurable diseases, including Parkinson's disease, various cancers, diabetes and spinal damage.

Stem cells refer to cells having not only self-replicating ability but also an ability to differentiate into at least two types of cells, and can be divided into totipotent stem cells, pluripotent stem cells, and multipotent stem cells (MSCs).

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are also called embryonic stem cells and can differentiate into various other tissue cells but cannot form new living organisms.

Multipotent stem cells were first isolated from adult bone marrow (Y. Jiang et al., Nature, 418: 41, 2002), and then also found in other various adult tissues (C. M. Verfaillie, Trends Cell Biol., 12: 502, 2002). In other words, although the bone marrow is the most widely known source of stem cells, the multipotent stem cells were also found in the skin, blood vessels, muscles and brains (J. G. Tomas et al., Nat. Cell Biol., 3: 778, 2001; M. Sampaolesi et al., Science, 301: 487, 2003; Y. Jiang et al., Exp. Hematol., 30: 896, 2002). However, stem cells in adult tissues, such as the bone marrow, are very rarely present, and such cells are difficult to culture without inducing differentiation, and thus difficult to culture in the absence of specifically screened media.

The reason why it is important to establish cell lines of such multipotent stem cells is because of the objectives of the research on the proliferation, lyophilization and characterization of stem cell lines, drug tests, and the autologous, allogeneic and xenogeneic transplantation of stem cell lines.

Also, animal models have been of particular importance in regenerative medicine for the repair or restoration of function of injured or damaged tissues. Over 370 genetic diseases have been found in canines and majority of these canine diseases resemble human diseases and dysfunctions. Thus, canines are of increasing importance as animal models for the research of the mechanism and pathogenesis of human genetic diseases, particularly X-linked severe combined immunodeficiency and combined genetic rare recessive diseases such as Duchenne muscular dystrophy, which are difficult to study directly in humans. Such canines are useful animal models for studying not only solid organ transplantation, but also for studying the pathogenic mechanisms of human diseases, including prostate cancer, cardiovascular diseases, bone regeneration, diabetes, leukemia and spinal cord injury, and for testing new therapeutic methods. In addition, canines are ideal large animal models for studying various therapeutic methods such as stem cell transplantation and gene therapies.

Therefore, isolation and characterization of stem cells derived from various canine tissues have become important issues in the stem cell field. Conventionally, there have been studies on stem cells from human and mouse tissues in various fields. As described above, canine aminals are useful large animal models for studying human diseases, but studies on canines have not yet been sufficient. Canine stem cells can be isolated from adipose tissue, bone marrow, umbilical cord blood and the like, but these are obtained in limited amounts, and the method of obtaining adipose tissue or bone marrow from individuals is invasive and causes pain.

In the current state of technology, in order to use stem cells as cell therapeutic agents, it is required to standardize the culture conditions under which an undifferentiated state can be maintained. In addition, because stem cells isolated from tissues are present as a mixture of various kinds of cells, it is required to develop technology capable of culturing homogeneous stem cells on a mass scale. In particular, methods for isolating stem cells from tissues or blood generally include, for example, cell sorting utilizing antibodies for a number of surface antigens. However, this method has a shortcoming in that the surface antigens of stem cells should be known. In addition, a common surface antigen (hereinafter referred to as "marker") for stem cells is not yet known. Also, various markers for stem cells have not been developed, and known markers for stem cells are expressed at different levels depending on the differentiation state of stem cells. Particularly, a system of sorting cells according to the expression level of the markers is expensive. Due to such shortcomings, the use of the cell sorting method has been greatly limited.

The placenta plays an important role in the development and survival of a fetus by supplying nutrients and oxygen thereto. Generally, the placenta is disposed of as medical waste after delivery. However, recent studies indicate that human amniotic tissue is a source rich in stem cells, and many studies on stem cells derived therefrom have been conducted. In clinical applications, amniotic tissue has effects on wound healing and retinal reconstitution. The amnion may possibly contain stem cells in a mixture with other monocytes and other stem cells. Under culture conditions for such mixed cells, the distribution of nutrients cannot be uniform, thereby causing heterogeneity in differentiation of cells. Conclusively, the problem that the cells cannot be produced as a homogeneous cell population serves as a fatal disadvantage, as when they are used as the therapeutic agent the actual effect may be different from the intended effect. Therefore, there is an urgent need for the development of effective culture technology that makes it possible to obtain homogeneous adult stem cells in a large quantity.

DISCLOSURE

Technical Problem

The present inventors first isolated a population of stem cells having increased homogeneity from a canine amniotic membrane, which is a new source of stem cells and is easily collected from female dogs after delivery. They have found that the stem cells have more rapid and continuous self-renewal ability (growth ability) than other stem cells and show the immunological characteristics of multipotent stem cells and have an excellent capability of differentiation into various cells, particularly into osteocytes, thereby completing the present invention.

Technical Solution

It is an object of the present invention to provide canine amniotic membrane-derived multipotent stem cells.

Another object of the present invention is to provide a method for preparing canine amniotic membrane-derived multipotent stem cells.

Still another object of the present invention is to provide a method for differentiating canine amniotic membrane-derived multipotent stem cells into various types of tissue cells.

Still another object of the present invention is to provide a cell therapeutic agent comprising canine amniotic membrane-derived multipotent stem cells or the tissue cells that differentiated therefrom, as an active ingredient.

Still another object of the present invention is to provide the use of canine amniotic membrane-derived multipotent stem cells or the tissue cells differentiated therefrom, for cell therapy.

Still another object of the present invention is to provide a method for treating a canine animal, comprising administering the cell therapeutic agent to a subject in need thereof.

Advantageous Effects

According to the present invention, it was found that the canine amniotic membrane can be used as a source of canine multipotent stem cells. The canine amniotic membrane-derived multipotent stem cells prepared according to the present invention shows excellent proliferation and differentiation capabilities, and thus can be used as an active ingredient in a cell therapeutic agent for veterinary regenerative medicine for canine animals and for large animal models in cell therapy for human diseases, which requires a large amount of stem cells.

DESCRIPTION OF DRAWINGS

FIG. 1 shows the primary culture of canine amniotic membrane-derived multipotent stem cells (cAM-MSCs) according to an example of the present invention, the cumulative population doubling level (CPDL) of the cells, and the expression level of stem cell-specific markers as a function of passage number. Specifically, FIG. 1A shows an isolated canine amniotic membrane tissue, FIG. 1B shows a phase contrast image of cAM-MSCs, FIG. 1C is a cell growth curve of cAM-MSCs, and FIGS. 1D to 1G show the expression levels of the stem cell-specific markers OCT4, SOX2, NANOG and KLF4 as a function of passage number.

FIG. 2 shows the results of FACS analysis of cAM-MSCs according to an example of the present invention. The analysis was performed at passage 5.

FIG. 3 shows the adipogenic differentiation of cAM-MSCs according to an example of the present invention. FIGS. 3A to 3D show the results of oil red O staining at 3 weeks after induction of adipogenesis. FIGS. 3A and 3B show control cells grown in a basal culture medium, and no oil red O staining was observed in the control cells. FIGS. 3C and 3D show cells treated with adipogenic induction medium for adipogenic differentiation. Fatty droplets in differentiated cells were stained with oil red O. The black arrow indicates stained red fatty droplets. FIG. 3E shows the results of quantification, obtained by eluting the dye with 100% isopropanol and measuring the absorbance at 500 nm by spectrophotometry for 0.5 seconds. The absorbance was 5 times higher in the differentiated cells than in the control cells. FIGS. 3F and 3G show the results of RT-PCR for specific markers of adipogenesis, FABP4, LEPTIN and LPL (F) and the gene expression levels by quantitative RT-PCR for the same (G). For mRNA quantification, GAPDH was used as a reference. All analyses were repeated three times and expressed as mean±standard deviation ($p<0.01$, *$p<0.001$).

FIG. 4 shows the ostengenic differentiation of cAM-MSCs according to an example of the present invention. FIGS. 4A to 4D show cells stained with Alizarin Red S after 3 weeks of culture, in order to confirm osteogenic differentiation. FIGS. 4A and 4B show control cells cultured in a basal culture medium, and no Alizarin Red S staining was observed in the cells. FIGS. 4C and 4D show cells grown in osteogenic induction medium, and the cells were strongly stained with Alizarin Red S compared to the control cells. FIG. 4E shows the results of quantification, obtained by eluting the dye with 100 mM cetylpyridinium chloride and measuring the absorbance at 570 nm by spectrophotometry for 0.5 seconds. All analyses were repeated three times. FIGS. 4F and 4G show the results of RT-PCR for specific markers of osteogenesis, MSX2, SPARC, COL1A1 and BGLAP (F) and the gene expression levels by quantitative RT-PCR for the same (G). For mRNA quantification, GAPDH was used as a reference. All analyses were repeated three times and expressed as mean±standard deviation (***$p<0.001$).

FIG. 5 shows the neurogenic differentiation of cAM-MSCs according to an example of the present invention. FIGS. 5A and 5B show control cells grown in a basal culture medium. The control cells showed positive response to GFAP, but not to beta-III tubulin. FIGS. 5C and 5D show cells stained with GFAP and beta-III tubulin after neurogenesis. FIGS. 5E to 5G show negative control cells stained with Alexa 488 (green, F), Alexa 594 (red, G) and Hoechst for nuclear detection (blue, E). FIGS. 5H and 5I show the results of RT-PCR for neuron-specific markers, MAP2 and GFAP (H) and the gene expression levels by quantitative RT-PCR for the same (I). For mRNA quantification, GAPDH was used as a reference. All analyses were repeated three times and expressed as mean±standard deviation (***p<0.001).

FIG. 6 shows the chondrogenic differentiation of cAM-MSCs according to an example of the present invention. 3 weeks after induction of chondrogenesis, the formation of a pellet was observed. FIG. 6A is an image of an oval chondrogenic pellet. The pellet was formed at the bottom of a 15 ml polypropylene tube. The black arrow indicates the pellet. FIG. 6B shows the result of toluidine blue staining of the chondrogenic pellet. The pellet was embedded in paraffin and cut into 3-mm sections, which were then mounted on a slide. The slide was stained with toluidine blue. The stained tissue showed a chondrogenic phenotype. FIGS. 6C and 6D show the results of RT-PCR for specific markers of chondrogenesis, AGGRECAN and COL2A by RT-PCR (C) and the gene expression levels by quantitative RT-PCR for the same (D). For mRNA quantification, GAPDH was used as a reference. All analyses were repeated three times and expressed as mean±standard deviation.

FIG. 7 shows the primary culture of cAM-MSC cell lines 2 and according to an example of the present invention, and the cumulative population doubling level (CPDL) of the cell lines, in order to confirm reproducibility. FIGS. 7A and 7B show canine amniotic membrane tissue isolated in order to prepare cell lines 2 and 3, and FIGS. 7C and 7D show phase contrast images of cAM-MSC cell lines 2 and 3. FIG. 7E shows cell growth curves of cell line 2 (solid line) and cell line 3 (dotted line).

FIG. 8 shows the adipogenic differentiation of cAM-MSC cell lines 2 and 3 according to an example of the present invention, in order to confirm reproducibility. FIGS. 8A to 8D show the results of oil red O staining at 3 weeks after induction of adipogenesis. FIGS. 8A and 8C show control cells grown in a basal culture medium, and no oil red staining was observed in the control cells. FIGS. 8B and 8D shows cells treated with adipogenic induction medium for adipogenic differentiation. Fatty droplets in differentiated cells were stained with oil red O. Scale bar=50 μm. FIGS. 8E and 8F show the results of quantification, obtained by eluting the dye with 100% isopropanol and measuring the absorbance 500 nm by spectrophotometry for 0.5 seconds. All analyses were repeated three times and expressed as mean±standard deviation (***; p<0.001). FIGS. 8G and 8H show the gene expression levels of specific markers of adipogenesis, FABP4, LEPTIN and LPL, by RT-PCR.

FIG. 9 shows the osteogenic differentiation of cAM-MSC cell lines 2 and 3 according to an example of the present invention, in order to confirm reproducibility. FIGS. 9A to 9D shows cells stained with Alizarin Red S after 3 weeks of culture in order to confirm osteogenic differentiation. FIGS. 9A and 9C show control cells cultured in a basal culture medium, and no Alizarin Red S staining was observed in the control cells. FIGS. 8B and 4D show cells grown in osteogenic induction medium, and the cells were strongly stained with Alizarin Red S compared to the control cells. Scale bar=50 μm. FIGS. 9E and 9F show the results of quantification, obtained by eluting the dye with 100 mM cetylpyridinium chloride and measuring the absorbance at 570 nm by spectrophotometry for 0.5 seconds. All analyses were repeated three times and expressed as mean±standard deviation (***; p<0.001). FIGS. 9G and 9H show the gene expression levels of specific markers of osteogenesis, MSX2, SPARC, COL1A1 and BGLAP, by RT-PCR.

FIG. 10 shows the neurogenic differentiation of cAM-MSC cell lines 2 and 3 according to an example of the present invention, in order to confirm reproducibility. FIGS. 10A and 10B show the gene expression levels of neuron-specific markers, MAP2 and GFAP, by RT-PCR.

FIG. 11 shows the chondrogenic differentiation of cAM-MSC cell lines 2 and 3 according to an example of the present invention, in order to confirm reproducibility. FIGS. 11A and 11D are images of oval chondrogenic pellets. The pellet was formed at the bottom of a 15 ml polypropylene tube. FIGS. 11B and 11E show the results of toluidine blue staining of the chondrogenic pellet. Scale bar=100 μm. FIGS. 11C and 11F show the gene expression levels of specific markers of chondrogenesis, AGGRECAN and COL2A, by RT-PCR.

BEST MODE

In order to accomplish the above objects, an aspect of the present invention provides a method for preparing canine amniotic membrane-derived multipotent stem cells, comprising the steps of: (1) isolating cells from a canine amniotic membrane; (2) culturing the isolated stem cells in low-glucose Dulbecco's modified Eagle medium (LG-DMEM); and (3) harvesting the cultured cells, wherein the canine amniotic membrane-derived multipotent stem cells are characterized by: (a) showing negative immunological responses to all of human markers CD3, CD11c, CD28, CD34, CD38, CD41a, CD45 and CD62L, and positive immunological responses to all of human markers CD90 and CD105; (b) having the ability to differentiate into ectoderm, mesoderm or endoderm-derived cells; and (c) having the ability to be maintained in an undifferentiated state for 20 passages or more.

Step (1) is a step of isolating cells from a canine amniotic membrane, which is a source rich in stem cells but which has been disposed of as medical waste. Isolation of the cells is performed by a slight modification of the method known in the art [Diaz-Prado, S. et al., *Tissue Eng. Part C Methods*, 2010; Mihu C. M. et al., *Rom. J. Morpho. Embryol.*, 50: 73-77, 2009], and all of placental samples used in the present invention are collected from a canine animal after Cesarean section delivery.

Step (1) comprises the sub-steps of: (i) degrading the amniotic membrane with an enzyme to remove an amniotic epithelial cell layer; and (ii) isolating single mesodermal cells from the amniotic membrane, from which the amniotic epithelial cell layer was removed, by a chemical method. Preferably, the enzyme in sub-step (i) may be trypsin-EDTA, and the chemical method in sub-step (ii) may be treatment with collagenase. More preferably, the enzyme that is used in sub-step (i) may be 0.25% trypsin-EDTA, and the enzyme that is used in sub-step (ii) may be collagenase type I, but the scope of the present invention is not limited thereto.

As used herein, the term "canine animals" refers to omnivorous animals, including dogs, wolves, foxes, coyotes, jackals, and Korean wolves, which are all digitigrade animals. The canine animals are broadly divided into Canini and Vulpini. Canini includes *Chrysocyon brachyurus, Canis adustus, Canis mesomelas, Canis lupus familiaris, Canis lupus dingo, Canis rufus, Canis simensis, Canis pallipes, Canis latrans, Canis aureus, Cerdocyon, Speothos, Cuon alpinus, Lycaon pictus, Atelocynus microtis, Dusicyon australis, Lycalopex culpaeus, Lycalopex fulvipes, Lycalopex*

*griseus, Lycalopex gymnocercus, Lycalopex sechurae, Lycalopex vetulus* and the like. Vulpini includes *Vulpes lagopus, Vulpes vulpes, Vulpes velox, Vulpes macrotis, Vulpes corsac, Vulpes chama, Vulpes pallid, Vulpes bengalensis, Vulpes ferrilata, Vulpes cana, Vulpes ruppelli, Vulpes zerda, Urocyon cinereoargenteus, Urocyon littoralis, Urocyon* sp and the like, and there are other animals such as *Otocyon megalotis, Nyctereutes procyonoides* and the like.

As used herein, the term "amniotic membrane" refers to a layer that forms a three-layer structure together with chorion and basalis to constitute the placenta. It is a thin, blood vessel-free membrane having a two-layer structure consisting of a simple epithelium and a basement membrane and is a sac that binds to a fetus to constitute an environment. The results of clinical studies indicate that amniotic membrane tissue is effective in wound healing and retinal reconstitution.

Step (2) is a step of culturing the isolated cells in low-glucose Dulbecco's modified Eagle medium (LG-DMEM). In this step, a population of stem cells with increased homogeneity is isolated and allowed to proliferate. The culturing in step (2) is preferably performed in such a manner that the cells adhere to the culture dish. Further, in step (2), the concentration of glucose in the low-glucose DMEM is 800-1200 mg/L, preferably 1000 mg/L. In addition, the low-glucose DMEM medium may contain fetal bovine serum, but is not limited thereto.

As used herein, the term "stem cells" refers to cells having not only self-replication ability but also the ability to differentiate into at least two types of cells. The stem cells can be divided into totipotent stem cells, pluripotent stem cells, and multipotent stem cells (MSCs). In order for cells to be considered as stem cells, the cells must continuously replicate in an undifferentiated state and must be able to differentiate into a specific type of cell under a specific culture condition. Due to their differentiation ability and self-renewal ability, the stem cells described above have recently received attention as a candidate as a composition for cell therapeutic agents, and many studies thereon have been conducted. It was found that canine amniotic membrane-derived multipotent stem cells according to the present invention can proliferate until 20 passages (FIG. 1C).

As used herein, the term "multipotent stem cells" refers to cells capable of differentiating only into specific types of cells that form a tissue and organ into which stem cells are introduced. It was found that canine amniotic membrane-derived multipotent stem cells according to the present invention have the ability to differentiate independently into adipocytes, osteocytes, neurocytes or chondrocytes depending on culture conditions (Examples 7 to 10; FIGS. 3 to 6).

The stem cells prepared in steps (1) and (2) of the method according to the present invention are characterized by showing negative immunological responses to all of the human markers CD3, CD11c, CD28, CD34, CD38, CD41a, CD45 and CD62L, and positive immunological responses to all of the human markers CD90 and CD105. Herein, the human marker CD90 is also called "Thy-1", which is a marker of several types of stem cells (skin-derived stem cells, endothelium-derived stem cells, and mesenchymal stem cells) [Masson N. M. et al., Am. J. Physiol. Gastrointest Liver Physiol., 290(1): G45-65, 2006], and the human marker CD105 is also known as endoglin that is a marker of MSCs [Dominici M. et al., *Cytotherapy*, 8(4): 315-7, 2006]. Meanwhile, the stem cells of the present invention do not have a positive response to the immune cell markers CD3, CD11c, CD28, CD38 and CD62L, the blood cell marker CD34 and the platelet marker CD41a. This suggests that the stem cells prepared according to the method of the present invention are multipotent stem cells.

According to an example of the present invention, it could be seen that the stem cells prepared according to the method of the present invention could differentiate into adipocytes, osteocytes, neurocytes or chondrocytes depending on culture conditions and could proliferate in an undifferentiated state until passage 20. This also suggests that the stem cells prepared according to the method of the present invention are multipotent stem cells.

Another aspect of the present invention provides a method for preparing homogeneous canine amniotic membrane-derived multipotent stem cells, comprising isolating multipotent stem cells, which show negative immunological responses to all of the human markers CD3, CD11c, CD28, CD34, CD38, CD41a, CD45 and CD62L, and positive immunological responses to all of the human markers CD90 and CD105, from cells isolated from a canine amniotic membrane, wherein the homogeneous canine amniotic membrane-derived multipotent stem cells are characterized by: (a) having the ability to differentiate into ectoderm, mesoderm or endoderm-derived cells; and (b) having the ability to be maintained in an undifferentiated state for 20 passages or more.

Isolation of the cells according to the above-described immunological characteristics is preferably performed using antibodies against the human markers, which show cross-reactivity between different species. Until now, specific antibodies for canine animals have not been found. Thus, in the present invention, the immunological phenotypes of multipotent stem cells isolated from the canine amniotic membrane are characterized using human-specific antibodies.

A further aspect of the present invention provides canine amniotic membrane-derived multipotent stem cells characterized by: (a) showing negative immunological responses to all of the human markers CD3, CD11c, CD28, CD34, CD38, CD41a, CD45 and CD62L, and positive immunological responses to all of the human markers CD90 and CD105; (b) having the ability to differentiate into ectoderm, mesoderm or endoderm-derived cells; and (c) having the ability to be maintained in an undifferentiated state for 20 passages or more. Preferably, the multipotent stem cells may be mesenchymal stem cells.

In one embodiment, the present invention provides a method for differentiating multipotent stem cells into adipocytes, comprising culturing the canine amniotic membrane-derived multipotent stem cells, prepared according to the method of the present invention, in a culture medium containing dexamethasone, indomethacin, 3-isobutyl-1-metyl-xanthine and insulin. Preferably, the medium that is used in the culturing may be an adipogenic differentiation medium containing 1 μM dexamethasone, 60 μM indomethacin, 500 μM 3-isobutyl-1-metyl-xanthine (IBMX) and 5 μg/ml insulin, but is not limited thereto.

As used herein, the term "adipocytes" refers to the cells that primarily compose adipose tissue specialized in storing energy as fat. There are two types of adipose cell: white fat cells that contain a large lipid droplet surrounded by a layer of cytoplasm; and polygonal brown fat cells that have considerable cytoplasm, with lipid droplets scattered throughout. White fat cells secrete proteins acting as adipokines such as resistin, adiponectin and leptin.

In another embodiment, the present invention provides a method for differentiating multipotent stem cells into osteocytes, comprising culturing the canine amniotic membrane-derived multipotent stem cells, prepared according to the method of the present invention, in a culture medium comprising ascorbic acid 2-phosphate, dexamethasone and beta-glycerophosphate. Preferably, the culture medium that is used in the culturing may be a osteogenic differentiation medium containing 50 µM ascorbic acid 2-phosphate, 100 nM dexamethasone, 10 mM β-glycerophosphate, and 10% fetal bovine serum in a low glucose-Dulbecco's modified Eagle medium (LG-DMEM), but is not limited thereto.

As used herein, the term "osteocytes" refers to star-shaped cells that are most abundantly present in dense bone tissue and that include a nucleus and a thin cytoplasmic ring. Osteoblasts are trapped in the matrix secreted by themselves and become osteocytes. Osteocytes are networked to each other via long cytoplasmic extensions that occupy tiny canals called canaliculi, which are used for exchange of nutrients and waste through gap junctions. Meanwhile, osteocytes have reduced synthetic activity, are not capable of mitotic division, and develop in mesenchyme, and hydroxyapatite, calcium carbonate and calcium phosphate are deposited around the cell.

In another embodiment, the present invention provides a method for differentiating multipotent stem cells into neurocytes, comprising culturing the canine amniotic membrane-derived multipotent stem cells, prepared according to the method of the present invention, in an induction medium comprising docosahexaenoic acid, B27 supplement and dimethyl sulfoxide following an incubation with beta-mercaptoethanol for 24 hours. Preferably, the cells may be incubated with beta-mercaptoethanol (1 mM; BME) and 5% FBS for 24 hours, and then cultured in a serum-free neurogenic induction medium containing 100 µM docosahexaenoic acid (DHA), B27 supplement and dimethyl sulfoxide (DMSO), but is not limited thereto.

As used herein, the term "neurocytes" refers to electrically excitable cells that process and transmit information by electrical and chemical signaling. Chemical signaling occurs via synapses, specialized connections with other cells. Neurocytes connect to each other to form networks. Neurocytes are the core component of the nervous system, which includes the brain, spinal cord, and peripheral ganglia.

In another embodiment, the present invention provides a method for differentiating multipotent stem cells into chondrocytes, comprising culturing the canine amniotic membrane-derived multipotent stem cells, prepared according to the method of the present invention, in chondrogenic differentiation medium. Preferably, the method may comprise seeding the cells into a propylene tube, centrifuging the tube to obtain pellets, and culturing the pellets in 1 ml of chondrogenic differentiation medium. The chondrogenic differentiation medium may be a medium containing TGF-β3, dexamethasone, ascorbate and the like, but is not limited thereto, and a commercially available medium may be used.

As used herein, the term "chondrocytes" refers to the only cells found in cartilage. Chondrocytes produce and maintain the cartilaginous matrix composed mainly of collagen and proteoglycan. The organization of chondrocytes in cartilage depends on the shape of cartilage and the location within the tissue.

A further aspect of the present invention provides a cell therapeutic agent, comprising the multipotent stem cells isolated from the canine amniotic membrane according to the method of the present invention, or the cells differentiated therefrom, as an active ingredient.

As used herein, the term "cell therapeutic agent" refers to a drug used for the purpose of treatment, diagnosis and prevention, which contains a cell or tissue prepared through isolation from humans, culture and specific operation (as provided by the US FDA). Specifically, it refers to a drug used for the purpose of treatment, diagnosis and prevention through a series of behaviors of in vitro multiplying and sorting living autologous, allogenic and xenogenic cells or changing the biological characteristics of cells by other means for recovering the functions of cells or tissues.

The cell therapeutic composition of the present invention may further comprise a pharmaceutically acceptable carrier. As used herein, the term "pharmaceutically acceptable" means a carrier that is non-toxic to cells or humans that are exposed to the composition. Examples of carriers that may be used in the present invention include, but are not limited to, buffers, preservatives, analgesics, solubilizing agents, isotonic agents, stabilizers, bases, excipients, lubricants, preservatives and the like. The pharmaceutical composition of the present invention can be formulated in various forms by a conventional technique known in the art. The cell therapeutic agent that is the composition of the present invention may be administered by any route through which it can be delivered to a disease site. In some cases, it can be contemplated to load the cell therapeutic agent into a vehicle comprising a means for delivering stem cells to a lesion. Thus, the composition of the present invention may be administered by various routes, including topical routes (including buccal, sublingual, skin and intraocular routes), parenteral routes (including subcutaneous, intracutaneous, intramuscular, instillation, intravenous, intra-arterial, intra-articular and intra-cerebrospinal routes) or a transdermal route. Preferably, it may be administered parenterally. Most preferably, it is administered directly to a disease site. In an embodiment, the stem cells may be administered to a subject in a state in which these cells are suspended in a suitable diluent at a concentration of about $1 \times 10^3$ to $5 \times 10^6$ cells/ml. Herein, the diluent is used to protect and maintain the cells and to facilitate the injection of the cells into a desired tissue. Examples of the diluent include physiological saline, buffer solution such as phosphate buffered saline or HBSS, plasma, cerebrospinal fluid, or blood components. In addition, the pharmaceutical composition may be administered by any device that can deliver the active ingredient to target cells. Preferred administration mode and formulation are injectable formulations. Injectable formulations can be prepared using aqueous solvents such as physiological saline, Ringer's solution, Hank's solution or sterile aqueous solution, vegetable oils such as olive oil, higher fatty acid esters such as ethyl oleate, or non-aqueous solvents such as ethanol, benzyl alcohol, propylene glycol, polyethylene glycol or glycerin. For transmucous administration, non-invasive agents suitable for a barrier through which the composition is to be passed may be used in formulation. Such non-invasive agents are generally known in the art. In addition, the composition may further comprise pharmaceutically acceptable carriers, including a stabilizer for preventing degeneration (e.g., ascorbic acid, sodium hydrogen sulfite, BHA, tocopherol, EDTA, etc.), an emulsifier, a buffering agent for pH control, and a preservative for inhibiting microbial growth (e.g., phenylmercury nitrate, thimerosal, benzalkonium chloride, phenol, cresol, benzylalcohol, etc.).

Preferably, the cell therapeutic agent can be used for the treatment of canine musculoskeletal diseases or nervous system diseases. More preferably, the cell therapeutic agent can be used for the treatment of canine osteoarthritis, for the treatment of canine bone loss disease, for the formation of canine adipose tissue, for the formation of canine tendon tissue, for the formation of canine muscle tissue, for formation of canine nervous tissue, for treatment of canine nervous system disease including spinal cord injury, for treatment of canine ophthalmologic disease including corneal or retinal disease, for treatment of canine intestinal tract disease, for treatment of canine atopic skin disease, or for treatment of canine autoimmune disease including lupus.

Therefore, the present invention provides the use of canine amniotic membrane-derived multipotent stem cells or tissue cells that differentiated therefrom, for cell therapy.

The present invention also provides a method for treating a canine animal, comprising administering the cell therapeutic agent to a subject in need thereof.

As used herein, the term "treating" refers to all actions that alleviate or beneficially change symptoms of a canine disease, for example, a disease caused by the injury or loss of muscle, cartilage, nerve or adipose tissue, by administering the composition of the present invention.

[Mode For Invention]

Hereinafter, the present invention will be described in further detail with reference to examples. It is to be understood, however, that these examples are illustrative purposes only and are not intended to limit the scope of the present invention.

The present invention was conducted in accordance with "the Guide for the Care and Use of Laboratory Animals" of Seoul National University (Korea), and performed in accordance with the policies and regulations of organizations and governments which are applicable to the ethical use of animals.

EXAMPLE 1

Collection of Canine Amniotic Membrane

Amniotic membranes, which were normally disposed of after separation by Cesarean section delivery, were used (the College of Veterinary Medicine, Seoul National University). These membranes were for research purposes only and were provided without cost. The separated membranes were used only for the isolation and characterization of stem cells from the tissue. In the present invention, healthy adult mixed-breed dogs (n=6; 4.5±0.4 kg) were used. Before Cesarean section delivery, the animals were treated with acepromazine maleate (0.1 mg; Sedaject, Samwoo medical, Yesan, Korea), and then thiopental sodium (15 mg; Pentotal, Joongwei pharmaceutical, Seoul, Korea) was injected intravenously for induction of anesthesia. Isoflurane (AErrane, Baxter, Mississauga, ON, Canada) was used for maintaining the anesthetic state. All procedures were performed under sterile conditions.

EXAMPLE 2

Isolation and Culture of Stem Cells

Cell isolation was performed by a slight modification of the previously described method [Diaz-Prado, S. et al., Tissue Eng. Part C Methods, 2010; Mihu C. M. et al., Rom. J. Morpho. Embryol, 50: 73-77, 2009]. All the placental samples were collected from canine animals through Cesarean section delivery by the method of Example 1. To separate the amniotic membrane from the whole placenta, the amniotic membrane was physically separated from the chorion. Under sterile conditions, the collected amniotic membrane was washed 3-4 times with physiological saline (0.9%). To remove epithelial cells, the collected amniotic membrane was treated with trypsin-EDTA (0.25%) at 37° C. for 30 minutes and washed 3-4 times with physiological saline. Then, the amniotic membrane from which epithelial cells were removed was cut into small pieces with a surgical knife and treated with collagenase type I (2 mg/ml; Worthington biochemical, Freehold, N.J.) at 37° C. for about 3-4 hours to separate into single mesodermal cells. Then, the cells were washed with phosphate buffered saline (PBS; Cellgro, USA) by centrifugation at 350 g for 5 minutes. After removing the supernatant, the cell pellets were resuspended in 10% FBS-containing low-glucose DMEM (LG-DMEM; Gibco BRL, USA), a basal medium. The cells were seeded into a 75T polystyrene culture flask (Nunc, USA) and incubated in a 5% $CO_2$ humidified incubator. The basal medium was replaced three times a week, and when a confluence of 80-90% was reached, the cells were subcultured. FIG. 1A shows the amniotic membrane separated from the canine placental tissue. cAM-MSCs isolated from the amniotic membrane showed the typical pyramidal shape of MSCs and adhered to the plastic culture dish (FIG. 1B).

EXAMPLE 3

Cumulative Population Doubling Level Analysis

Stem cells, including multipotent stem cells, have self-renewal capacity which is associated with continuous and steady proliferation rate [Reya T. et al., Nature, 414(6859): 105-11, 2001]. Therefore, the proliferation and growth efficiency of the cAM-MSCs obtained in Example 2 were determined based on the total cumulative population doubling level using the formula CPDL=ln(Nf/Ni)ln 2, wherein Ni is the initial seeding cell number, Nf is the final harvest cell number, and ln is the natural log. The cells ($5\times10^4$) were seeded into three 6-well culture plates (Nunc), and after 5-7 days, subcultured. The number of final cells was counted, and $5\times10^4$ cells were re-seeded. To determine the cumulative population doubling level, the population doubling level of each passage was calculated and added to the previous population doubling level. This procedure was repeated from passage 3 to passage 20 where the proliferation rate started to decrease. The results are shown in FIG. 1C.

In addition, in order to measure the gene expression levels of stem cell-specific markers, quantitative RT-PCR was performed in a passage-dependent manner. A specific experimental method is described in Example 5 below. In the present invention, stem cell-specific markers such as OCT4, SOX2, NANOG and KLF4 are used. As a result, as shown in FIGS. 1D to 1G, the expression levels of the stem cell markers decreased as the number of passages increased.

EXAMPLE 4

RT-PCR

In the present invention, cAM-MSCs, isolated and cultured in Example 2, were differentiated into various types of tissue cells, and then the gene expression levels of markers associated with differentiation into each tissue were analyzed by RT-PCR. The experiment was performed in the following manner, and the results of the experiment were presented together with the results of each differentiation experiment. Total RNA was extracted from the cultured cells using the Easy-Spin total RNA extraction kit (Intron Biotechnology, Seongnam, Korea) according to the manufacturer's instructions. The absorbance was measured at 260 nm by a spectrophotometer to determine the RNA concentration. cDNA was prepared by 1 μg of total RNA for reverse transcription using Superscript II reverse transcriptase (Invitrogen, Carlsbad, Calif.) and oligo (dT) primers (Invitrogen). The cDNA was amplified by PCR using Platinum Taq (Invitrogen, Carlsbad, Calif.). The PCR primers are shown in Table 2. The PCR products were separated on 1.5% agarose gel and visualized with ethidium bromide.

EXAMPLE 5

Quantitative RT-PCR

In the present invention, the gene expression levels of stem cell-specific markers for cAM-MSCs isolated and cultured in Example 2 and markers associated with differentiation into each tissue for the various types of tissue cells differentiated therefrom were analyzed by quantitative RT-PCR. The experiment was performed in the following manner, and the results of the experiment were presented together with the results of each differentiation experiment. Quantitative RT-PCR was performed by mixing cDNA with primers and Power SYBR Green PCR Master Mix (Applied Biosystems, Foster City, Calif.). Quantitative RT-PCR was performed using an ABI 7500 Realtime-PCR System with supplied software (Applied Biosystems), according to the manufacturer's instructions. RNA expression levels were compared after normalization to endogenous glyceraldehyde-3-phosphate dehydrogenase (GAPDH). The primer sequences used in the present invention are listed in Tables 1 and 2.

TABLE 1

List of quantitative RT-PCR primers for stem cell-specific markers

| Name | Sequence of primers | Temp. (° C.) | SEQ. ID. # |
|------|---------------------|--------------|------------|
| OCT4 | Forward: TCGTGAAGCCGGACAAGGAGAAG | 60 | 1 |
|      | Reverse: AGGAACATGTTCTCCAGGTTGCCT |    | 2 |
| SOX2 | Forward: AACCCCAAGATGCACAACTC | 60 | 3 |
|      | Reverse: CGGGGCCGGTATTTATAATC |    | 4 |
| NANOG | Forward: CCTGCATCCTTGCCAATGTC | 60 | 5 |
|       | Reverse: TCCGGGCTGTCCTGAGTAAG |    | 6 |
| KLF4 | Forward: CCATGGGCCAAACTACCCAC | 60 | 7 |
|      | Reverse: TGGGGTCAACACCATTCCGT |    | 8 |

TABLE 2

List of PCR primers for differentiation markers

| Markers | Name | Sequence of primers | Size | Cycle | Temp. (° C.) | SEQ. ID. # |
|---------|------|---------------------|------|-------|--------------|------------|
| Adipocyte | LPL | Forward: ACACATTCACAAGAGGGTCAC | 132 | 32 | 60 | 9 |
|           |     | Reverse: CTCTGCAATCACACGGATG |     |    |    | 10 |
|           | LEPTIN | Forward: CTATCTGTCCTGTGTTGAAGCTG | 102 | 32 | 60 | 11 |
|           |        | Reverse: TGTGTGAAATGTCATTGATCCTG |     |    |    | 12 |
|           | FABP4 | Forward: ATCAGTGTAAACGGGGATGTG | 117 | 32 | 60 | 13 |
|           |       | Reverse: GACTTTTCTGTCATCCGCAGTA |     |    |    | 14 |
| Osteocyte | SPARC | Forward: TGAGAAGGTATGCAGCAACG | 110 | 32 | 56 | 15 |
|           |       | Reverse: AGTCCAGGTGGAGTTTGTGG |     |    |    | 16 |
|           | MSX2 | Forward: TCCGCCAGAAACAATACCTC | 243 | 32 | 56 | 17 |
|           |      | Reverse: AAGGGTAGGACGCTCCGTAT |     |    |    | 18 |
|           | COL1A1 | Forward: CACCTCAGGAGAAGGCTCAC | 134 | 32 | 56 | 19 |
|           |        | Reverse: ATGTTCTCGATCTGCTGGCT |     |    |    | 20 |
|           | BGLAP | Forward: GTGGTGCAACCTTCGTGTC | 132 | 34 | 58 | 21 |
|           |       | Reverse: GCTCGCATACTTCCCTCTTG |     |    |    | 22 |
| Neurocyte | GFAP | Forward: TCCGAGGGGGCAAAAGCACC | 104 | 30 | 62 | 23 |
|           |      | Reverse: GGCAGGCTGCTAACCGAGAGC |     |    |    | 24 |
|           | MAP2 | Forward: CAGCGACAAGGCCGACACGT | 336 | 34 | 66 | 25 |
|           |      | Reverse: GGGCCAAACTCGACACCCGG |     |    |    | 26 |

TABLE 2-continued

List of PCR primers for differentiation markers

| Markers | Name | Sequence of primers | Size | Cycle | Temp. (° C.) | SEQ. ID. # |
|---|---|---|---|---|---|---|
| Chondro-cyte | COL2A1 | Froward: GAAACTCTGCCACCCG AATG | 156 | 34 | 64 | 27 |
| | | Reverse: GCTCCACCAGTTCTTC TTGG | | | | 28 |
| | AGGRECAN | Forward: ATCACAGTGCTTACCA AGACA | 122 | 32 | 60 | 29 |
| | | Reverse: ATAACCTCACAGCGAT AGATCC | | | | 30 |
| House-keeping | GAPDH | Forward: AACATCATCCCTGCTT CCAC | 392 | 24 | 58 | 31 |
| | | Reverse: TCCTTGGAGGCCATGT AGAC | | | | 32 |

EXAMPLE 6

Immunophenotypic Characterization of cAM-MSCs by Flow Cytometry

Generally, human MSCs have distinguishable, specific surface antigen markers. According to the International Society of Cellular Therapy, human MSCs generally show positive responses to the human markers CD73, CD44, CD90 and CD105 and negative responses to the human markers CD11b, CD14, CD18, CD79a, CD34, CD45 and HLA-DR [Dominici M. et al., Cytotherapy, 8(4): 315-7, 2006]. Thus, to determine the immunophenotype of cAM-MSCs, an experiment on 10 CD markers was performed in the following manner.

First, cells were stained with specific antibodies for FACS analysis, following the protocol provided by the supplier (BD Biosciences, USA). Briefly, the cAM-MSCs were trypsinized and washed several times with PBS. The suspended cells were aliquoted (approximately $1 \times 10^6$ cells) for specific antibody staining. The cells were immunostained with the following antibodies: Mouse anti-human CD3, mouse anti-human CD11c, mouse anti-human CD28, mouse anti-human CD34, mouse anti-human CD38, mouse anti-human CD41a, mouse anti-human CD45, mouse anti-human CD62L, mouse anti-human CD90 (BD Biosciences) and mouse anti-human CD105 (Serotec, USA). The antibodies were conjugated with Fluorescein isothiocyanate (FITC) or phycoerythrin (PE). Analysis was performed by the use of FACS Calibur (BD Biosciences) and Cell Quest Pro (BD Biosciences) software.

As a result, it was shown that the cAM-MSCs have an expression pattern consistent with the MSC immunophenotype (FIG. 2). The cAM-MSCs showed positive response to CD90 and CD105, well-known and typical MSCs markers. CD90 is called Thy-1 and is a marker for various types of stem cells, such as endometrial stem cells, hepatic stem cells, keratinocyte stem cells and mesenchymal stem cells. CD105 is also called SH2 and is a well-known MSC marker. However, the stem cells of the present invention were negative for the expression of other immune cell markers (CD3, CD11c, CD28, CD38 and CD62L), hematopoietic cell markers (CD34 and CD45) and platelet marker (CD41a). These results show that the immunophenotype of the cAM-MSCs is consistent with that of other characterized MSCs.

EXAMPLE 7

Possibility of Differentiation into Adipocytes

In order to determine whether the cAM-MSCs prepared in Example 2 can differentiate into adipocytes, the cells were treated with an adipogenic differentiation medium containing dexamethasone (1 μM), indomethacin (60 μM), 3-isobutyl-1-metyl-xanthine (IBMX; 500 μM) and insulin (5 μg/ml) (Sigma-Aldrich, USA) for 3 weeks. For a control group, a basal culture medium was used. When a confluence of 80-90% was reached, the cells were treated with an adipogenic differentiation medium for 3 weeks. After 3 weeks, the cells were stained with Oil Red 0 for the detection of fatty droplets. The cells were fixed with 10% formalin for at least one hour and washed with 60% isopropanol before they were incubated in freshly diluted oil red O for 10 minutes. The dye was eluted with 100% isopropanol, and the absorbance at 500 nm was measured by a spectrophotometer.

As a result, fatty droplets formed under the differentiation condition could be detected, and no fatty droplet was detected under the control condition (FIGS. 3A to 3D). To quantify the differentiation status of the cells, oil red O was eluted from the cells, its absorbance was measured and then the result was shown in FIG. 3E. The differentiated cells displayed absorbance values that were 5-fold greater than those of the control cells. In addition, the present inventors measured the gene expression levels of markers associated with adipogenesis, such as FABP4, Leptin and LPL by RT-PCR (FIG. 3F) and quantitative RT-PCR (FIG. 3G). After differentiation, the expression of adipogenesis-associated markers was increased in treated cells with differentiation medium compared to control cells.

EXAMPLE 8

Possibility of Differentiation into Osteocytes

In order to determine whether the cAM-MSCs prepared in Example 2 can differentiate into osteocytes, an osteogenic differentiation medium containing ascorbic acid 2-phosphate (50 μM), dexamethasone (100 nM), β-glycerophosphate (10 mM) (Sigma-Aldrich, USA) and 10% fetal bovine serum (FBS) in low-glucose Dulbecco's Modified Eagle Medium (LG-DMEM) was used. For a control group, a basal culture medium was used. When a confluence of 80-90% was reached, the medium was replaced with an osteogenic differentiation medium, and then the cells were incubated for 3 weeks. After 3 weeks, Alizarin Red S staining, which positively respond to calcium depositions, was used to detect a calcium deposition. The cells were washed with PBS and fixed with ice-cold ethanol (70%) for 1 hour at 4° C. The cells were then washed 3-4 times with distilled water. The cells were stained with Alizarin Red S (40 mM; pH 4.2; Sigma-Aldrich, USA) for 10 min at room temperature. The cells were washed five times with distilled water to remove non-specifically adsorbed dye. Alizarin Red S dye was solubilized using cetylpyridinium chloride (100 mM; Sigma-Aldrich, USA) for 1 hour. Absorbance of solubilized Alizarin Red S was measured at 570 nm using a spectrophotometer.

As a result, under differentiation conditions, there was strong, positive Alizarin Red S staining. Negative staining was observed under control conditions (FIGS. 4A to 4D). To quantify the differentiation status, stain was eluted from the cells with 100 mM of cetylpyridinium chloride and absorbance thereof measured. The differentiated cells displayed about 15-fold greater values than control cells (FIG. 4E). Additionally, the present inventors measured the gene expression levels of markers associated with osteogenesis, such as MSX2, SPARC, COL1A1 and BGLAP by RT-PCR (FIG. 4F) and quantitative RT-PCR (FIG. 4G). After differentiation, the expressions of the osteogenesis-associated markers were increased compared to controls.

EXAMPLE 9

Possibility of Differentiation into Neurocytes

Neurogenesis of the cAM-MSCs prepared in Example 2 was induced using a neuronal differentiation medium. For a control group, a basal culture medium was used. The cells were seeded in the basal culture medium and allowed to reach confluence. To induce differentiation, the cells were incubated with Beta-mercaptoethanol (1 mM; BME Sigma-Aldrich, USA) and 5% FBS for 24 hours prior to induction. Then, the cells were treated with serum-free induction medium containing docosahexaenoic acid (100 µM; DHA, Sigma-Aldrich, USA), B27 supplement (Gibco BRL, USA) and 1.5% dimethyl sulfoxide (DMSO, Sigma-Aldrich, USA) for 2 days. Differentiation was analyzed by immunostaining and RT-PCR. The immunostaining method is described in detail in Example 11 below.

As a result, neural markers GFAP and beta III tubulin were positively expressed under differentiation conditions (FIGS. 5C and 5D). However, under the basal culture condition, cAM-MSCs expressed GFAP but, not beta III tubulin (FIGS. 5A and 5B). The negative control was incubated with secondary antibodies Alexa 488 & 594, but demonstrated no background signal (FIGS. 5E and 5F). When the expression levels of nerve-associated genes by RT-PCR (FIG. 5H) and quantitative RT-PCR (FIG. 5I) were measured, it was found that GFAP was expressed under both control and neural differentiation conditions. Under differentiation conditions, MAP2 expression was positive compared to control conditions (FIGS. 5H and 5I).

EXAMPLE 10

Possibility of Differentiation into Chondrocytes

To promote the chondrogenic differentiation of the cAM-MSCs prepared in Example 2, a chondrogenic differentiation medium was used. For a control group, a basal culture medium was used. The cells ($5\times10^5$) were seeded in a 15 ml polypropylene tube and centrifuged to obtain a pellet. The cell pellets were cultured by incubating in 1 ml of chondrogenic differentiation medium (Lonza) for 3 weeks. The medium was changed 3 times a week. After differentiation, the pellets were embedded in paraffin and cut to 3 µm sections. To detect chondrogenesis, the sections were stained with toluidine blue according to standard protocols.

As a result, it was found that the pellet formed at the bottom of the polypropylene tube had an ovoid shape and an opaque body (FIG. 6A). Toluidine blue staining was performed to identify chondrogenesis. After differentiation, the pellet showed positive toluidine blue staining (FIG. 6B). The present inventors also measured the expression patterns of genes associated with chondrogenic markers, such as Aggrecan and COL2A1 by RT-PCR (FIG. 6C) and quantitative RT-PCR (FIG. 6D). The expression of chondrogenic markers was increased under differentiation conditions, compared to control conditions (FIGS. 6C and 6D).

EXAMPLE 11

Immunostaining

Mouse anti-neuron specific beta III tubulin (Abcam, UK) and rabbit anti-Glial Fibrillary Acidic Protein (GFAP, Millipore, USA) antibodies were used for immunostaining. Cells were fixed with 4% paraformaldehyde for 20 min, and were then permeabilized in 0.5% Triton-X 100 at room temperature for 10 min. After washing 3-4 times with PBS, the cells were blocked with 10% normal goat serum (NGS) overnight at 4° C. The cells were incubated with primary antibodies for 2 hours at room temperature. After washing with PBS, the cells were incubated with secondary antibodies Alexa 488 & 594 (1:1000, Molecular Probe, Inc., Eugene, Oreg., USA) for 1 hour. Finally, for nuclear staining, the samples were incubated for 15 minutes with Hoechst 33238 (1 mg/ml), diluted 1:100 in PBS. Images were captured using a confocal microscope (Eclipse TE2000; Nikon, Japan).

EXAMPLE 12

Verification of Reproducibility

In order to verify the reproducibility of the method for isolating and culturing stem cells according to the present invention, the present inventors isolated and cultured cells from 6 different canine amniotic membrane samples according to the methods described in Examples 1 and 2 (the rate of success was 100%). All the isolated cells from 6 samples showed a very similar cell morphology and ability to be subcultured. Among them, three cell lines were randomly selected, a single cell line was further selected, and the independently isolated and cultured stem cells were characterized according to the methods described in Examples 3 to 11. All experiments were repeatedly conducted by only the selected cell lines three times. The results of characterization of additional cell lines 2 and 3 are shown in FIGS. 7 to 11 and Table 3 below. As a result, it was found that the patterns of cell morphology, CPDL (cumulative population doubling level), adipogenic, osteogenic, chondrogenic and neurogenic differentiation, and immunophenotypes for cell lines 2 and 3 were similar to those for cell line 1 shown in FIGS. 1 to 6. This suggests that the canine amniotic membrane-derived stem cells, isolated and cultured according to the method of the present invention, are multipotent stem cells, show the immunophenotypes of multipotent mesenchymal stem cells and can differentiate into various types of tissue cells.

TABLE 3

| CD markers | Cell Line-2 | Cell Line-3 |
| --- | --- | --- |
| CD3 | 1.28% | 0.42% |
| CD11c | 0.96% | 0.8% |
| CD28 | 1.25% | 0.35% |
| CD34 | 2.29% | 0.41% |
| CD38 | 0.81% | 0.56% |
| CD41a | 1.23% | 1.84% |
| CD45 | 0.6% | 0.46% |
| CD62L | 0.93% | 0.41% |
| CD90 | 100% | 100% |
| CD105 | 99.85% | 99.48% |

The invention claimed is:

1. A method for producing canine amniotic membrane-derived multipotent stem cells comprising the steps of:
   (1) isolating cells from a canine amniotic membrane;
   (2) culturing the isolated cells in low glucose Dulbecco's modified Eagle medium (LG-DMEM); and
   (3) harvesting the cultured cells,
   wherein the equine amniotic membrane-derived multipotent stem cells cultured by the step (2) are selected for;
   (a) showing negative immunological responses to all of human markers CD19, CD20, CD28, CD31, CD34, CD38, CD41a, CD62L, CD62P and CD200, and positive immunological responses to all of human markers CD44, CD90 and CD105; and
   (b) having the ability to be maintained in an undifferentiated state for 14 passages or more.

2. The method of claim 1, wherein step (1) comprises the sub-steps:
   (i) degrading the amniotic membrane with an enzyme to remove an amniotic epithelial cell layer; and
   (ii) isolating single mesodermal cells from the amniotic membrane, from which the amniotic epithelial cell layer was removed, by a chemical method.

3. The method of claim 2, wherein the enzyme that is used in sub-step (i) is trypsin-EDTA.

4. The method of claim 2, wherein the chemical method in sub-step (ii) is a treatment with collagenase type I.

5. The method of claim 1, wherein step (2) is performed by adherent culture.

6. The method of claim 1, wherein the LG-DMEM in the step (2) has a glucose concentration of 800-1200 mg/L.

7. The method of claim 1, wherein the LG-DMEM in the step (2) further contains fetal bovine serum.

8. The method of claim 1, wherein the canine is any one selected from the group consisting of dogs, wolves (*Canis lupus*), *Canis rufus*, *Canis latrans* (coyote), jackals, foxes, bush dogs, raccoons (*Nyctereutes procyonoides*), *Lycaon, Chrysocyon*, Australian dingo, and *Cuon*.

9. The method of claim 1 wherein the stem cells are mesenchymal stem cells.

10. A method for differentiating multipotent stem cells into adipocytes, comprising culturing the multipotent stem cells prepared by the method of claim 1 in a culture medium comprising dexamethasone, indomethacin, 3-isobutyl-1-methyl-xanthine, and insulin.

11. A method for differentiating multipotent stem cells into osteocytes, comprising culturing the multipotent stem cells prepared by the method of claim 1 in a culture medium comprising ascorbic acid 2-phosphate, dexamethasone and beta-glycerophosphate.

12. A method for differentiating multipotent stem cells into neurocytes, comprising culturing the multipotent stem cells prepared by the method of claim 1 in an induction medium comprising docosahexaenoic acid, B27 supplement and dimethyl sulfoxide following an incubation with beta-mercaptoethanol for 24 hours.

13. A method for differentiating multipotent stem cells into chondrocytes, comprising culturing the multipotent stem cells prepared by the method of claim 1 in a chondrogenic differentiation medium.

14. A method for treating a canine animal, comprising the steps of:
   (1) isolating cells from a canine amniotic membrane;
   (2) culturing the isolated cells in low glucose Dulbecco's modified Eagle medium (LG-DMEM);
   (3) harvesting the cultured cells; and
   (4) administering the harvested cells the canine animal, wherein the canine amniotic membrane-derived multipotent stem cells cultured by the step (2) are selected for:
   (a) showing negative immunological responses to all of human markers CD19, CD20, CD28, CD31, CD34, CD38, CD41a, CD62L, CD62P and CD200, and positive immunological responses to all of human markers CD44, CD90 and CD105; and
   (b) having the ability to be maintained in an undifferentiated state for 14 passages or more.

15. The method of claim 14, wherein the harvested cells are administered to the canine animal to treat canine osteoarthritis, canine bone loss disease, canine nervous system disease including spinal cord injury, canine ophthalmologic disease including corneal or retinal disease, canine intestinal tract disease, canine atopic skin disease, or canine autoimmune disease including lupus, or wherein the harvested cells are administered to the canine animal to promote formation of canine adipose tissue, canine tendon tissue, canine muscle tissue, or canine nervous tissue.

* * * * *

SEQUENCE LISTING

<160> NUMBER OF SEQ ID NOS: 32

<210> SEQ ID NO 1
<211> LENGTH: 23
<212> TYPE: DNA
<213> ORGANISM: Artificial Sequence
<220> FEATURE:
<223> OTHER INFORMATION: OCT4 forward

<400> SEQUENCE: 1
tcgtgaagcc ggacaaggag aag                                             23

<210> SEQ ID NO 2
<211> LENGTH: 24
<212> TYPE: DNA
<213> ORGANISM: Artificial Sequence
<220> FEATURE:
<223> OTHER INFORMATION: OCT4 reverse

<400> SEQUENCE: 2
aggaacatgt tctccaggtt gcct                                            24

<210> SEQ ID NO 3
<211> LENGTH: 20
<212> TYPE: DNA
<213> ORGANISM: Artificial Sequence
<220> FEATURE:
<223> OTHER INFORMATION: SOX2 forward

<400> SEQUENCE: 3
aaccccaaga tgcacaactc                                                 20

<210> SEQ ID NO 4
<211> LENGTH: 20
<212> TYPE: DNA
<213> ORGANISM: Artificial Sequence
<220> FEATURE:
<223> OTHER INFORMATION: SOX2 reverse

<400> SEQUENCE: 4
cggggccggt atttataatc                                                 20

<210> SEQ ID NO 5
<211> LENGTH: 20
<212> TYPE: DNA
<213> ORGANISM: Artificial Sequence
<220> FEATURE:
<223> OTHER INFORMATION: NANOG forward

<400> SEQUENCE: 5
cctgcatcct tgccaatgtc                                                 20

<210> SEQ ID NO 6

```
<211> LENGTH: 20
<212> TYPE: DNA
<213> ORGANISM: Artificial Sequence
<220> FEATURE:
<223> OTHER INFORMATION: NANOG reverse

<400> SEQUENCE: 6
tccgggctgt cctgagtaag                                              20

<210> SEQ ID NO 7
<211> LENGTH: 20
<212> TYPE: DNA
<213> ORGANISM: Artificial Sequence
<220> FEATURE:
<223> OTHER INFORMATION: KLF4 forward

<400> SEQUENCE: 7
ccatgggcca aactacccac                                              20

<210> SEQ ID NO 8
<211> LENGTH: 20
<212> TYPE: DNA
<213> ORGANISM: Artificial Sequence
<220> FEATURE:
<223> OTHER INFORMATION: KLF4 reverse

<400> SEQUENCE: 8
tggggtcaac accattccgt                                              20

<210> SEQ ID NO 9
<211> LENGTH: 21
<212> TYPE: DNA
<213> ORGANISM: Artificial Sequence
<220> FEATURE:
<223> OTHER INFORMATION: LPL forward

<400> SEQUENCE: 9
acacattcac aagagggtca c                                            21

<210> SEQ ID NO 10
<211> LENGTH: 19
<212> TYPE: DNA
<213> ORGANISM: Artificial Sequence
<220> FEATURE:
<223> OTHER INFORMATION: LPL reverse

<400> SEQUENCE: 10
ctctgcaatc acacggatg                                               19

<210> SEQ ID NO 11
<211> LENGTH: 23
<212> TYPE: DNA
<213> ORGANISM: Artificial Sequence
<220> FEATURE:
<223> OTHER INFORMATION: LEPTIN forward

<400> SEQUENCE: 11
ctatctgtcc tgtgttgaag ctg                                          23

<210> SEQ ID NO 12
<211> LENGTH: 23
<212> TYPE: DNA
<213> ORGANISM: Artificial Sequence
<220> FEATURE:
<223> OTHER INFORMATION: LEPTIN reverse

<400> SEQUENCE: 12
```

```
tgtgtgaaat gtcattgatc ctg                                              23
```

<210> SEQ ID NO 13
<211> LENGTH: 21
<212> TYPE: DNA
<213> ORGANISM: Artificial Sequence
<220> FEATURE:
<223> OTHER INFORMATION: FABP4 forward

<400> SEQUENCE: 13

```
atcagtgtaa acggggatgt g                                                21
```

<210> SEQ ID NO 14
<211> LENGTH: 22
<212> TYPE: DNA
<213> ORGANISM: Artificial Sequence
<220> FEATURE:
<223> OTHER INFORMATION: FABP4 reverse

<400> SEQUENCE: 14

```
gacttttctg tcatccgcag ta                                               22
```

<210> SEQ ID NO 15
<211> LENGTH: 20
<212> TYPE: DNA
<213> ORGANISM: Artificial Sequence
<220> FEATURE:
<223> OTHER INFORMATION: SPARC forward

<400> SEQUENCE: 15

```
tgagaaggta tgcagcaacg                                                  20
```

<210> SEQ ID NO 16
<211> LENGTH: 20
<212> TYPE: DNA
<213> ORGANISM: Artificial Sequence
<220> FEATURE:
<223> OTHER INFORMATION: SPARC reverse

<400> SEQUENCE: 16

```
agtccaggtg gagtttgtgg                                                  20
```

<210> SEQ ID NO 17
<211> LENGTH: 20
<212> TYPE: DNA
<213> ORGANISM: Artificial Sequence
<220> FEATURE:
<223> OTHER INFORMATION: MSX2 forward

<400> SEQUENCE: 17

```
tccgccagaa acaataccte                                                  20
```

<210> SEQ ID NO 18
<211> LENGTH: 20
<212> TYPE: DNA
<213> ORGANISM: Artificial Sequence
<220> FEATURE:
<223> OTHER INFORMATION: MSX2 reverse

<400> SEQUENCE: 18

```
aagggtagga cgctccgtat                                                  20
```

<210> SEQ ID NO 19
<211> LENGTH: 20
<212> TYPE: DNA

```
<213> ORGANISM: Artificial Sequence
<220> FEATURE:
<223> OTHER INFORMATION: COL1A1 forward

<400> SEQUENCE: 19
cacctcagga gaaggctcac                                              20

<210> SEQ ID NO 20
<211> LENGTH: 20
<212> TYPE: DNA
<213> ORGANISM: Artificial Sequence
<220> FEATURE:
<223> OTHER INFORMATION: COL1A1 reverse

<400> SEQUENCE: 20
atgttctcga tctgctggct                                              20

<210> SEQ ID NO 21
<211> LENGTH: 19
<212> TYPE: DNA
<213> ORGANISM: Artificial Sequence
<220> FEATURE:
<223> OTHER INFORMATION: BGLAP forward

<400> SEQUENCE: 21
gtggtgcaac cttcgtgtc                                               19

<210> SEQ ID NO 22
<211> LENGTH: 20
<212> TYPE: DNA
<213> ORGANISM: Artificial Sequence
<220> FEATURE:
<223> OTHER INFORMATION: BGLAP reverse

<400> SEQUENCE: 22
gctcgcatac ttccctcttg                                              20

<210> SEQ ID NO 23
<211> LENGTH: 20
<212> TYPE: DNA
<213> ORGANISM: Artificial Sequence
<220> FEATURE:
<223> OTHER INFORMATION: GFAP forward

<400> SEQUENCE: 23
tccgaggggg caaaagcacc                                              20

<210> SEQ ID NO 24
<211> LENGTH: 21
<212> TYPE: DNA
<213> ORGANISM: Artificial Sequence
<220> FEATURE:
<223> OTHER INFORMATION: GFAP reverse

<400> SEQUENCE: 24
ggcaggctgc taaccgagag c                                            21

<210> SEQ ID NO 25
<211> LENGTH: 20
<212> TYPE: DNA
<213> ORGANISM: Artificial Sequence
<220> FEATURE:
<223> OTHER INFORMATION: MAP2 forward

<400> SEQUENCE: 25
cagcgacaag gccgacacgt                                              20
```

```
<210> SEQ ID NO 26
<211> LENGTH: 20
<212> TYPE: DNA
<213> ORGANISM: Artificial Sequence
<220> FEATURE:
<223> OTHER INFORMATION: MAP2 reverse

<400> SEQUENCE: 26
gggccaaact cgacacccgg                                                  20

<210> SEQ ID NO 27
<211> LENGTH: 21
<212> TYPE: DNA
<213> ORGANISM: Artificial Sequence
<220> FEATURE:
<223> OTHER INFORMATION: COL2A1 forward

<400> SEQUENCE: 27
gaaactctgc caccctgaat g                                                21

<210> SEQ ID NO 28
<211> LENGTH: 20
<212> TYPE: DNA
<213> ORGANISM: Artificial Sequence
<220> FEATURE:
<223> OTHER INFORMATION: COL2A1 reverse

<400> SEQUENCE: 28
gctccaccag ttcttcttgg                                                  20

<210> SEQ ID NO 29
<211> LENGTH: 22
<212> TYPE: DNA
<213> ORGANISM: Artificial Sequence
<220> FEATURE:
<223> OTHER INFORMATION: AGGRECAN forward

<400> SEQUENCE: 29
atcaacagtg cttaccaaga ca                                               22

<210> SEQ ID NO 30
<211> LENGTH: 22
<212> TYPE: DNA
<213> ORGANISM: Artificial Sequence
<220> FEATURE:
<223> OTHER INFORMATION: AGGRECAN reverse

<400> SEQUENCE: 30
ataacctcac agcgatagat cc                                               22

<210> SEQ ID NO 31
<211> LENGTH: 20
<212> TYPE: DNA
<213> ORGANISM: Artificial Sequence
<220> FEATURE:
<223> OTHER INFORMATION: GAPDH forward

<400> SEQUENCE: 31
aacatcatcc ctgcttccac                                                  20

<210> SEQ ID NO 32
<211> LENGTH: 20
<212> TYPE: DNA
<213> ORGANISM: Artificial Sequence
<220> FEATURE:
```

```
<223> OTHER INFORMATION: GAPDH reverse

<400> SEQUENCE: 32
tccttggagg ccatgtagac                                                    20
```